United States Patent [19]
Stiefel et al.

[11] Patent Number: 5,231,081
[45] Date of Patent: Jul. 27, 1993

[54] USE OF HEMOCYANINS AND ARYLPHORINS TO INFLUENCE THE IMMUNE SYSTEM AND FOR THE TREATMENT OF TUMORS

[76] Inventors: Thomas Stiefel, Steinkopfstrasse 22, 7000 Stuttgart 1; Harald Porcher, Uhlbacherstrasse 7, 7000 Stuttgart 61; Jürgen Markl, Hildastrasse 24, 6900 Heidelberg, all of Fed. Rep. of Germany

[21] Appl. No.: 780,386

[22] Filed: Oct. 23, 1991

Related U.S. Application Data

[63] Continuation of Ser. No. 284,696, Dec. 15, 1988, abandoned.

[30] Foreign Application Priority Data

Dec. 17, 1987 [EP] European Pat. Off. ........ 87118765.4

[51] Int. Cl.$^5$ ............................................. A61K 37/14
[52] U.S. Cl. ........................................... 514/6; 514/21
[58] Field of Search ...................................... 514/6, 21

[56] References Cited

PUBLICATIONS

Telfer et al., *Annu. Rev. Entomol.*, "The Function and Evolution of Insect Storage Hexamers," 36:205-228 (1991).
Nguyen et al., *J. Biological Chem.*, "The Amino Acid Sequence of Limulus C-reactive Protein," vol. 261, No. 22, pp. 10456-10465 (1986).
Puppione et al., *Biochimica et Biophysica Acta*, "Physicochemical Study of Rock Crab Lipoproteins," 875:563-568 (1986).
Miyata et al., *J. Biological Chem.*, "Amino Acid Sequence of the Coagulogen From Limulus Polyphemus Hemocytes," vol. 259, No. 14, pp. 8924-8933 (1984).
Duman et al., *Ann. Rev. Physiol.*, "The Role of Hemolymph Proteins in the Cold Tolerence of Insects," 45:261-270 (1983).
Engelmann, *Adv. Insect Physiol.*, "Insect Vitellogenin: Identification, Biosynthesis, and Role in Vitellogenesis," 14:49-108 (1979).
Lamy et al. Hoppe-Seyler Z. Physiol. Chem. Bd. 360, S. 889-895, Jul. 1979.
G. C. deGast et al. Acta Med. Scand. vol. 194, pp. 303-309 (1973).
Denizot et al. Cellular Immunology 58, 333-344 (1981).
Kempter et al. Biol. Chem. Hoppe-Seyler vol. 366 pp. 77-86, Jan. 1985.
Markl et al. Hoppe-Seyler's Z. Physiol. Chem. Bd. 363, S. 73-87 Jan. 1982.
Lontie Life Chem. Rep. Suppl. 1 109-120, 1983.
Drexel et al., *Complete Amino-Acid Sequence of a Functional Unit from a Molluscan Hemocyanin (Helix pomatia)*, 1987, Biol. Chem. H.S. 368, pp. 617-635.
Richards, *The Protein Folding Problem*, 1991, Scientific American, pp. 54-63.

*Primary Examiner*—Michael G. Wityshyn
*Assistant Examiner*—Choon Koh
*Attorney, Agent, or Firm*—Rothwell, Figg, Ernst & Kurz

[57] ABSTRACT

The invention deals with the use of hemocyanin, other than keyhole-limpet hemocyanin, arylphorin, or a combination thereof to influence the immune system and for the treatment of tumors.

47 Claims, No Drawings

USE OF HEMOCYANINS AND ARYLPHORINS TO INFLUENCE THE IMMUNE SYSTEM AND FOR THE TREATMENT OF TUMORS

This is a continuation of application Ser. No. 07/284,696, filed Dec. 15, 1988, now abandoned.

FIELD OF THE INVENTION

The invention deals with the use of hemocyanins and arylphorins to influence the immune system and for the treatment of tumors.

BACKGROUND OF THE INVENTION

Hemocyanins are the principal serum proteins of many mollusks and arthropods. Hemocyanin is a blue copper protein responsible for the transport of oxygen. Its concentration in the blood is 20–120 mg/ml. It occurs among mollusks in snails (class of Gastropoda), inkfishes (class of Cephalopoda), chitons (class of Polyplacophora), elephant tooth snails (class of Scaphopoda) and mussels (class of Bivalvia). It has been found among arthropods in scorpions and spiders (class of Arachnida), horseshoe crabs (class of Xiphosura), shrimps, lobsters, crabs and crayfishes (class of Crustacea) and centipedes (class of Myriopoda).

Arylphorin is a principal protein of insects (class of Hexapoda) and is characterized by its high phenylalanine and tyrosine content. A concentration of up to 60 mg/ml is found in the larvae and pupae of holometabolic insects and in lower concentrations also in adult Holometabola and Hemimetabola. There is a special name for the arylphorins of each animal species (drosophilin, calliphorin, etc.). Arylphorins do not bind oxygen. Various functions as transporters of substances and cuticular components have been discussed. It was recently found, for example, in the course of studies on monoclonal antibodies, that arylphorins are structurally homologous with the hemocyanins of arthropods and are probably derivatives thereof.

Hemocyanins and arylphorins are synthesized in special cells. These cells, at least during their biogenesis, do not float freely in the blood circulation, but are associated with certain tissues that are in contact with the blood (cardiac muscle septa, intestinal gland, fat body, sinus of the eye, etc.). Hemocyanins and arylphorins are concentrated in these cells and released into the blood. Native snail hemocyanin is cylindrical, and with 35 nm has the volume of a polio virus. The other mollusk hemocyanins are half this size. Arthropod hemocyanins and arylphorins are structurally based on a cube with a side length of 10 nm. This cube may be halved in arylphorins, while in hemocyanins it is often oligomerized. The largest arthropod hemocyanin (Limulus) consists of 8 cubes and has a side length of 25 nm, which roughly corresponds to the size of a ribosome.

Arthropod hemocyanins and arylphorins consist of up to 8 immunologically different subunits having a molecular weight of around 70–80,000. The 10 nm basic cube is a hexamer made up of such subunits. Each type of subunit plays a specific structural part in oligohexameric hemocyanins. There are several complete sequence analyses in existence, as well as a detailed roentgen structural model. Many details of the genetic structure of arylphorins are known.

Hemocyanins and arylphorins can be broken down into subunits by dialysis against an alkaline pH and removal of divalent cations. In mollusks, this subunit consists of 7–8 globular domains, each of which has a molecular weight of around 55,000. The domains are immunologically very different. One of them has been completely sequenced. Each has an active, oxygen-binding center, consisting of 2 copper atoms. Up to 160 such domains are present in the native molecule. Their arrangement in the 35 nm particle is known in detail.

Based on the structural heterogeneity described, and its completely xenogeneic nature, since mollusks and arthropods have been separated from vertebrates as protostomia for at least 600 million years, hemocyanin is one of the strongest antigens known. In mammalians it leads to the formation of a very powerful antiserum, moves the T4/T8 ratio in favor of the T4 helper cells and at the site of application leads to local erythema and invasion by macrophages. This has been used for many years in immunologic research with keyhole limpet hemocyanin (KLH).

It is known that KLH gives rise to cytotoxic T-cells and has distinct antitumor effects in vitro and in various animal models in vivo. This quality of KLH has been repeatedly demonstrated. Clinical treatment with KLH leads to a significant drop in the rate of recurrence in cases of superficial bladder carcinoma, while unpleasant side effects have never been observed, and other types of tumors have also been positively affected (C. D. Jurincic et al. *Uroscope*, Information u. Fortbildung i.d. Urologie, issue 1, 1986). The exact mechanism of action of KLH on bladder carcinoma cells is not as yet entirely clear. It has been found, however, that the site of action is completely different from existing chemotherapeutic sites. The results of chemotherapy are partially contradictory. While cytotoxic drugs attack all urothelial cells, KLH stimulates the macrophages of the entire organism (J. E. Curtis et al. "Antigen dose in human immune response relationships in the human immune response to keyhole-limpet hemocyanin." *Journal of Laboratory in Clin. Med.*, 78:61 1971). Curtis has shown that KLH brings about both a primary cell-mediated, delayed hypersensitivity and a primary antibody response in humans.

This potent antigen thus acts as a nonspecific stimulant that activates T-lymphocytes and lymphokine-producing macrophages.

It was the task of this invention to make available additional powerful antigens of the same class of substances with an equal or stronger effect.

The task is solved by use of hemocyanin, other than keyhole-limpet hemocyanin, and/or arylphorin, to influence the immune system and for the treatment of tumors.

SUMMARY OF THE INVENTION

The invention deals with the use of hemocyanin, other than keyhole-limpet hemocyanin, arylphorin, or a combination thereof to influence the immune system and for the treatment of tumors.

It is known that keyhole-limpet hemocyanin has an antitumoral action on superficial bladder carcinoma. Hemocyanins and arylphorins isolated preferably from animals of the Calliphora, Helix, Octopus, Astacus, Carcinus, Limulus and Eurypelma species showed unexpected immunologic and tumor-inhibiting effects, especially when coupled with other components.

DETAILED DESCRIPTION OF THE INVENTION

In testing great variety of hemocyanins and arylphorins for their tumor growth-inhibiting action, it was found surprisingly that the hemocyanins and arylphorins of various animal groups show distinct immunologic differences and a varying intensity of antitumoral effect. In view of this, other valuable substances of the hemocyanin and arylphorin class can be used in addition to keyhole-limpet hemocyanin, for their favorable effect on the immune system and in the treatment of tumors. In particular, tumor types other than bladder carcinoma, known for the use of keyhole-limpet hemocyanin, can be treated with these substances. As has already been mentioned, the antitumoral mechanism of action of hemocyanin is not known. However, hemocyanins have a partial structure that is strikingly similar to that of the basic structure of immune globulins and MHC proteins. This, together with the effect on the immune system already referred to, may be the reason for the mode of action. The antitumoral effect of various hemocyanins was tested on methyl-cholanthrene-induced mouse fibrosarcoma. The data obtained allow the conclusion that hemocyanin and arylphorin prophylactically increase immune competence.

Hemocyanin and arylphorin are isolated from mollusk or arthropod tissues by selecting the individual types of mollusks or arthropoda from a group comprising the species Eurypelma, Limulus, Astacus, Carcinus, Calliphora, Helix and Octopus. The species cited are undoubtedly not the only species among mollusks or arthropods from which hemocyanins or arylphorins can be isolated having an effect on the immune system and a tumor growth-inhibiting effect.

The results obtained with the substances derived from the species tested are shown in Table 1. An antitumoral effect was present in every case, but was found to be distinctly stronger in native components than, for example, in components denatured with SDS.

To isolate the hemocyanins or arylphorins of the species referred to, the blood of the mollusks or arthropoda is drawn by puncture of extremities, blood lacunae or the heart, and the blood cells are centrifuged, thus preventing coagulation. From the supernatant obtained in this manner, the plasma, hemocyanins or arylphorins are purified from smaller hemolymph components by pelleting in the preparative ultracentrifuge, and redissolved in PBS. The resulting hemocyanin or arylphorin preparation is up to 95% pure. 100% purity can be achieved by subsequent anion exchange chromatography. Additional purification of arylphorins from other serum proteins can be achieved by dialysis at a pH value of 9.6 (glycine/OH buffer, 10 mM EDTA), whereupon the arylphorin is then dissociated into subunits. By subsequent anion exchange chromatography, 100% pure arylphorin is obtained, which can be reconstructed into the hexamer by dialysis against a neutral buffer (tris/HCl).

The hemocyanins used in this invention should originate preferably from the species Eurypelma californicum, Helix pomatia, Octopus vulgaris, Astacus fluviatilis, Carcinus maenas or Limulus polyphemus.

A preferred arylphorin originates from calliphora erythrocephala.

Preparations made from the animal species cited are available in 0.1 M tris/HCl buffer of pH 7.5. The dose is $3 \times 100$ μg in 0.5 ml PBS administered subcutaneously per animal and per day, to two sites (groin or axilla). Tumor cells used were syngeneic meth-A-sarcoma cells cultured in ascites cells from an in vivo passage. The cells were tested with tryptophane-blue (2% positive). $1 \times 10^5$ cells were implanted intracutaneously. Treatment with a hemocyanin from one of the preferred animal species cited above took place on days +2, +5 and +7, with 100 μg administered subcutaneously. Table 1 shows the results relating to tumor volumes and the rate of survival after 4 weeks. As is shown by Table 1, in the untreated control group none of the 10 animals outlived the period of 28 days after tumor implantation, while in the groups treated with hemocyanins, between 6 and 2 of 10 animals survived this period and the tumor volume after 28 days measured 11 and 34% of that of the untreated control group.

TABLE 1

| Hemocyanin Arylphorin source | 7 days tumor vol. cc | % | 14 days tumor vol. cc | % | 21 days tumor vol. cc | % | 28 days tumor vol. cc | % | Surviving animals |
|---|---|---|---|---|---|---|---|---|---|
| Eurypelma | 13.7 | 107 | 6.4 | 27 | 5.6 | 11 | 20.1 | 16 | 5/10 |
| Limulus | 13.4 | 105 | 8.1 | 34 | 5.1 | 10 | 13.8 | 11 | 6/10 |
| Astacus | 13.7 | 106 | 9.3 | 39 | 9.2 | 18 | 30.1 | 24 | 2/10 |
| Carcinus | 17.8 | 139 | 13.1 | 55 | 16.4 | 32 | 42.6 | 34 | 5/10 |
| Calliphora | 13.9 | 109 | 10.0 | 42 | 12.8 | 25 | 38.8 | 31 | 3/10 |
| Helix | 12.2 | 95 | 7.6 | 32 | 7.1 | 14 | 21.3 | 17 | 6/10 |
| Octopus | 14.6 | 114 | 6.9 | 29 | 5.6 | 11 | 17.5 | 14 | 5/10 |
| Eurypelma a | 13.8 | 108 | 17.6 | 74 | 27.6 | 54 | 80.2 | 64 | 2/10 |
| Eurypelma d | 13.1 | 102 | 19.8 | 83 | 34.8 | 68 | 101.5 | 81 | 0/10 |
| Eurypelma e | 10.6 | 83 | 15.7 | 66 | 24.5 | 48 | 68.9 | 55 | 2/10 |
| Helix d | 12.3 | 96 | 15.5 | 65 | 28.6 | 56 | 89.0 | 71 | 0/10 |
| Helix g | 14.7 | 115 | 17.1 | 72 | 31.2 | 61 | 77.7 | 62 | 1/10 |
| Eurypelma d SDS | 15.6 | 122 | 20.5 | 86 | 36.3 | 71 | 104.0 | 83 | 0/10 |
| Helix d SDS | 15.1 | 118 | 18.8 | 79 | 34.8 | 68 | 99.0 | 79 | 0/10 |
| Eurypelma d Tn34 | 13.2 | 103 | 23.3 | 98 | 53.7 | 105 | 150.4 | 120 | 0/10 |
| Eurypelma d Tn37 | 12.7 | 99 | 17.6 | 74 | 36.8 | 72 | 111.5 | 89 | 0/10 |
| Carcinus x Ec-8 antigen | 13.7 | 107 | 8.1 | 34 | 7.2 | 14 | 21.3 | 17 | 6/10 |
| Calliphora x Ec-8 antigen | 17.2 | 134 | 10.0 | 42 | 11.2 | 22 | 35.1 | 28 | 3/10 |
| Octopus x Ec-8 antigen | 11.8 | 92 | 5.5 | 23 | 4.1 | 8 | 15.0 | 12 | 6/10 |
| Eurypelma x meth-A-fragments | 14.1 | 110 | 4.5 | 19 | 3.6 | 7 | 11.3 | 9 | 8/10 |
| Carcinus (preimmun. w. Helix) | 11.1 | 87 | 7.6 | 32 | 5.6 | 11 | 15.0 | 12 | 7/10 |
| Octopus (preimmun. w. Calliphora) | 13.8 | 108 | 6.4 | 27 | 4.6 | 9 | 16.3 | 13 | 8/10 |
| Control | 12.8 | 100 | 23.8 | 100 | 51.1 | 100 | 125.3 | 100 | 0/10 |

The regrowth of tumor volumes after 28 days is attributed to the fact that treatment was broken off after 7 days and experience has shown that successful immunologic treatment persists only for about 2 weeks.

Subunits containing antigenic domains of complete hemocyanins or arylphorins can also be advantageously used. As was referred to in the introduction, molluscan hemocyanins are made up of subunits comprising 7 to 8 globular domains, each having a molecular weight of around 55,000. The arthropod hemocyanins and arylphorins may contain up to 8 immunologically different subunits with molecular weights of around 70-80,000. Since the subunits or domains are immunologically very diverse, it was surprising that all subunits or domains studied showed some effectiveness.

Preferred subunits are a, d and/or e of Eurypelma californicum hemocyanin. But as is shown in Table 1, the mechanism of action of the subunit d remains unclear, even though an effect was observed in reducing the tumor volume. The results clearly allow the conclusion that effectiveness can be assured for the subunit d as well.

The preferred use of the domains d and/or c of $\beta c$ hemocyanin from Helix pomatia also shows an inhibiting action on tumor growth after 14 and 21 days.

The subunit a of Eurypelma californicum hemocyanin can also be split with chymotrypsin. From the cleavage mixture a peptide fragment can be obtained consisting of 23 amino acids, which is predestined for an immunologic effect of the type required.

The peptide referred to, containing 23 amino acids, may be bound preferably to hemocyanin from Carcinus or Octopus, or arylphorin from Calliphora. The action of these coupled peptide subunits containing 23 amino acids is shown in Table 1 and it can be seen that this version of the invention in particular has an enormous effect, since in addition to a drastic reduction in the size of tumors, a high survival rate of 7 or 8 out of 10 animals has been observed.

Intensification of the required effects can also be achieved when complete hemocyanins or arylphorins, or the subunits described, are coupled either in mixtures, or chemically or physically with other components, which may consist of viruses or virus components, bacteria or bacterial components, fungi or their components, or animal parasites or their components. Such coupling has the advantage that it allows direct inoculation.

A further preferred use of the hemocyanins and arylphorins or their subunits used according to this invention consists of physical or chemical coupling with antigens before administration, with the object of increasing antibodies, or the reaction of the cellular immune system against the coupled substances.

A particularly strong effect is achieved when the substances referred to are coupled with meth-A-sarcoma tumor cell fragments. As is shown in Table 1, with this coupling, an enormous tumor-reducing effect, as well as an effect enhancing the chances of survival is also achieved.

The invention is explained in more detail on the basis of the following examples:

EXAMPLE 1

Isolation of hemocyanins and arylphorins.

Mollusk or arthropod blood is obtained by puncture of extremities, blood lacunae or the heart, and the blood cells are centrifuged, preventing coagulation. From the supernatant (=plasma) hemocyanins or arylphorins are purified of smaller hemolymph components by pelleting in the preparative ultracentrifuge, and then redissolving in PBS (phosphate buffered saline). The resulting hemocyanin preparation is up to more than 95% pure. 100% purity can be achieved by subsequent anion exchange chromatography. Pelleted arylphorin is more contaminated, since it binds other serum proteins loosely. These bonds can be broken up by dissociating arylphorin into subunits at pH 9.6 (glycine buffer, 10 mE EDT.A). Subsequent anion exchange chromatography yields 100% pure arylphorin, which can be reconstructed to the hexamer by dialysis against neutral buffer (tris/HCl).

EXAMPLE 2

The antitumoral effectiveness of various hemocyanins was tested on methylcholanthrene-induced mouse fibrosarcoma. The model has been described, for example, in: P. G. Munder et al.: "Antitumoral action of xenogeneic substances in vivo and in vitro", Onkologie 5, 4-7, 1982. The arylphorin of the blue-bottle fly Calliphora erythrocephala, and the hemocyanins of the following animals were used; Helix pomatia (edible snail) Octopus vulgaris (octopus), Astacus fluviatilis (river crayfish), Carcinus maenas (sand crab), Limulus polyphemus (horseshoe crab), and Eurypelma californicum (tarantula). All preparations were in 0.1 M tris/HCl buffer of pH 7.5. The dose was $3 \times 100$ µg in 0.5 ml PBS per animal and per day administered subcutaneously at two sites (groin and axilla). Tumor cells used were syngeneic meth-A-sarcoma tumor cells cultured in ascites from an in vivo passage. The cells were tested with tryptophane blue (2% positive). $1 \times 10^5$ cells were implanted intracutaneously. Treatment with hemocyanin took place on days +2, +5, and 7, with 100 µg administered subcutaneously. Table 1 shows the results relating to tumor volume and the rate of survival after 4 weeks. As can be seen, in the untreated control group none of 10 animals survived beyond the period of 28 days after tumor implantation, while in the hemocyanin groups between 6 and 2 of 10 animals survived this period and the tumor volumes were 11% and 34% of those of the untreated control groups after 28 days. The effect was the least marked with crustacean hemocyanins, which is attributed to the smaller number of subunit types and thus of antigen-determinants (J. Markl: "Evolution and function or structurally diverse subunits in the respiratory protein hemocyanin from arthropods", Biol. Bull. 171, 90-115, 1986).

EXAMPLE 3 a) The subunits a, d and e of Eurypelma californicum hemocyanin and the domains d and g of $\beta c$-hemocyanin of the edible snail Helix pomatia were isolated in the native state according to a published method (J. Markl et al: "Hemocyanins in spiders. VI. Comparison of the polypeptide chains of Eurypelma californicum hemocyanin". Hoppe-Seyler's Z. Physiol. Chem., 360, 639-650, 1979; R. Lontie: "Components, functional units, and active sites of Helix pomatia hemocyanin", Life Chem. Rep. Suppl. 1, 109-120, 1983), and their antitumoral action was tested on the meth-A-sarcoma model.

b) The subunit d of the tarantula and the d domain of the snail were also used in the SDS-denatured state (denaturation in 2% SDS. SDS was reduced to 0.1% by dialysis before administration to mice).

c) The native subunit d of the tarantula was split by limited trypsinolysis into two almost identical-sized fragments with a molecular weight of 34,000 and 37,000 and the fragments were isolated as described (Schartau et al.: "Hemocyanins in spiders, XIX, Complete amino-acid sequence of subunit d from Eurypelma californicum hemocyanin, and comparison to chain e. *Hoppe-Seyler's Z. Physiol. Chem.* 364, 1383–1409, 1984). These two denatured peptide fragments designated as dTn34 and dTn37 were also tested on the meth-A-sarcoma model.

All results are shown in Table 1. An antitumoral effect was present in every case, but was distinctly more marked with the native components than the denatured components. In the case of the subunit d from the spider, no definite difference was observed between the intact polypeptide chain and the C-terminal peptide fragment dTn37, while the N-terminal peptide fragment dTn34 was distinctly lower. Overall, the action of isolated components is undoubtedly weaker than that of complete hemocyanins from example 2.

d) Finally a peptide consisting of 23 amino acids was isolated from the chymotryptic cleavage mixture of subunit a by immune-affinity chromatography, by means of the sequence-bound monoclonal antibody Ec-8 recently described (J. Markl: "Characterization of monoclonal antibodies to tarantula hemocyanin", *Verh. Dtsch. Zool. Ges.* 80, in press, 1987), which is specifically directed against the tarantula subunit a, and carries the antigen determinant corresponding to Ec-8. This isolated antigen was coupled to the hemocyanins of Carcinus and Octopus, and the arylphorin of Calliphora by standard methods (J. W. Palreyman et al.: "Guidelines of the production of polypeptide specific antisera using small synthetic oligopeptides as immunogens", *J. Immunol. Meth.* 75, 383–393, 1984) and tested in this form on the meth-A-sarcoma model. The antitumoral effectiveness of the three carrier molecules on which the Ec-8 epitope does not occur was increased thereby (Table 1).

EXAMPLE 4

Possibilities of diagnostic evaluation of hemocyanins and arylphorins were tested on Eurypelma (tarantula), Carcinus (sand crab) and Octopus, hemocyanins, as well as the arylphorin of Calliphora (blue-bottle fly). The test is a B-cell function assay, carried out by measurement of the antibody titers after subcutaneous injection as neoantigen in guinea pigs. Two control animals were compared with two animals whose immune reaction was suppressed by cyclosporine (6.25 mg/kg body weight, 2× daily for 30 days). For the method, see P. O. Amlot et al., "Human immune response in vivo to protein (KLH) and polysaccharide (DNP-Ficoll) neoantigens: normal subjects compared with bone marrow transplant patients on cyclosporine", *Clin. Exp. Immunol.* 64, 125–135, 1986. The antibody titer was determined with an ELISA with 1 ng hemocyanin or arylphorin per microtiter-well, using anti-(guinea pig IgM) and anti-(guinea pig-IgG) coupled with alkaline phosphatase as second antiserum. The four substances tested fulfilled all criteria postulated by P.0. Amlot et al., and proved to be suitable for diagnosis of immune deficiency. The very good usability of KLH for the diagnosis of immune deficiency and other immunologic parameters thus surprisingly appears to apply to all hemocyanins and arylphorins.

EXAMPLE 5

The hemocyanins of the tarantula Eurypelma, the sand crab Carcinus, and the Octopus, and the arylphorin of the blue-bottle fly Calliphora were coupled partly with the commercially available substances cited below, and partly with substances from other sources, by methods described in the literature (Palfreyman et al., "Guidelines of the production of polypeptide specific antisera using small synthetic oligopeptides as immunogens", *J. Immunol. Meth.* 75, 383–393, 1984, and Jan Dahmen et al., "Synthesis of spacer-arm, lipid and ethyl glycosides of the terminal trisaccharide ($\alpha$-D-Gal (1->4) - $\beta$-D-Gal(1->4) - $\beta$-D-GLcNAc) portion of the blood-group $P_1$ antigen: preparation of neoglycoproteins", *Carbohydrate Research*, 129, 63–71, 1984; Jan Dahmen et al.: "Synthesis from pullulan of spacer-arm lipid, and ethyl glycosides of a tetrasaccharide ($\alpha$->D-GLc-(1 ->6) -$\alpha$-D-GLc-(1->D-GLc(1->4)-D-GLc) found in human urine; preparation of neoglycoproteins", *Carbohydrate Research*, 127, 27–33, 1984; Jan Dahmen et al.: "Synthesis of spacer-arm, lipid and ethyl glycosides of the trisaccharide portion ($\alpha$-D-Gal-(1->4)- $\beta$-D-Gal-(1->4)-$\beta$-D-GLc) of the blood group $p^k$ antigen: preparation of neoglycoproteins", Carbohydrate Research 127, 15–25, 1984; Jan Dahmen et al.: "2-bromoethyl glycosides in glycoside synthesis: Preparation of glycoproteins containing $\alpha$-L-Fuc-(1->2) -D-Gal and $\beta$-D-Gal - (1->4) -D-GLcNAc", *Carbohydrate Research* 125, 237–245, 1984; R. U. Lemieux, D. A. Baker and D. R. Bundle: "A Methodology for the production of carbohydrate-specific antibody", *Can. J. Biochem.* 55, 1977; J. D. Aplin, J. C. Wriston, Jr.: "Preparation, properties and applications of carbohydrate conjugates or proteins and lipids", *CRC Critical Reviews in Biochemistry*, p. 259, 1981; B. M. Pinto and Dr. R. Bundle: "Preparation of glycoconjugates from use as artificial antigens: A simplified procedure", *Carbohydrate Research* 124, 313–318, 1984).

a) Ganglioside GM2/GS3
b) Chymotryptic fragment cocktail of meth-A-Sarcoma tumor cells
c) Virus fragment (herpes virus)
d) Bacterial fragment (BCG, muramyl dipeptide)
e) Fungus fragments of Cryptococcus neoformans.
f) Schistosomula surface antigen of Schistosoma mansoni.

By administration to mice (three-fold standard immunization over 6 weeks) a strong, haptene-specific antiserum was obtained with the syngeneic meth-A-sarcoma cultured in ascites fragments as well. In order to demonstrate a combination therapeutic effect, acting on the one hand through immune modulatory and antitumoral mechanisms of hemocyanin itself, and on the other through specific anti-haptene antibodies, the procedure was as follows: Eurypelma hemocyanin was coupled with tumor cell fragments from meth-A-sarcoma and tested on the meth-A-sarcoma tumor model. The result in Table 1 shows an increase in the therapeutic effect compared to treatment with pure Eurypelma hemocyanin. After 28 days, 8 out of 10 mice survived. Thus the combination of hemocyanin as unspecific adjuvant with a specific antigen component has proved to be a more effective inoculum (with regard to the principle, see V. Schirrmacher: "Postoperative activation of tumor-specific T-cells as a means to achieve immune control of minimal residual disease", General Motors Cancer Research Foundation, *Accomplishments in Cancer Research* 1986, Fortner and Roads (eds), pp. 218–232).

EXAMPLE 6

To demonstrate general strengthening of the immune system, 10 mice were immunized over a period of 6 weeks by three subcutaneous applications of 0.1 mg Helix pomatia hemocyanin. After a further 3 weeks, meth-A-ascites tumor cells were implanted as in Example 2, and the mice were next treated with Carcinus hemocyanin (there are no immunologic cross reactions between mollusk and arthropod hemocyanin). Conversely, 10 mice were pretreated with Calliphora arylphorin and after implantation of tumor cells, treated with Octopus hemocyanin. In both cases the result of treatment was distinctly better than in the animals without pretreatment, as can be seen from Table 1. Measurements from immunization experiments on guinea pigs with Limulus, Eurypelma, Carcinus, Octopus and Helix hemocyanins, and Calliphora arylphorin, showed massive expansion of macrophages and T4 helper cells after application. Overall, the data allow the conclusion that hemocyanin and arylphorin prophylactically increase immune competence.

EXAMPLE 7

The use of hemocyanin from Carcinus and Octopus and the arylphorins of Calliphora as haptene carrier (Ec-8-specific peptide fragment as haptene) with the object of obtaining a reaction of the cellular immune system has already been described in the last section of Example 3. Parallel therewith, this haptene was injected with the 3 carriers to two guinea pigs (3× over a period of 6 weeks 0.1 mg subcutaneously). The result in each case was a strong antiserum not only against the carrier molecule, but also against the haptene. Two control animals having received only the haptene showed a negative reaction. The reaction of the haptene in the positive animals could easily be immunologically distinguished from the carrier molecule, since it was a tarantula-specific epitope. The IgG fraction directed against the haptene was isolated by affinity purification on BrCN Sepharose CL-4B coupled with tarantula hemocyanin, and the immune blot showed a highly specific reaction with the subunit a. Further data on this subject are provided by Examples 4 and 5.

We claim:

1. A method for the treatment of tumors in a warm animal, comprising administering to a warm blooded animal an arthropod hemocyanin, arylphorin or a combination thereof in an amount effective to elicit a nonspecific immune response in said warm blooded animal.

2. Method as claimed in claim 1, wherein the hemocyanin or arylphorin is isolated from tissues of arthropods, the arthropods being selected from a group consisting of the species Eurypelma, Limulus, Astacus, Carcinus, and Calliphora.

3. Method as claimed in claim 2, wherein a hemocyanin of Eurypelma californicum (tarantula) is used.

4. Method as claimed in claim 2, wherein a hemocyanin of Astacus fluviatilis (river crayfish) is used.

5. Method as claimed in claim 2, wherein a hemocyanin of Carcinus maenas (shore crab) is used.

6. Method as claimed in claim 2, wherein a hemocyanin of Limulus polyphemus (horseshoe crab) is used.

7. Method as claimed in claim 2, wherein an arylphorin of Calliphora erythrocephala (blue-bottle fly) is used.

8. Method as claimed in claim 1, wherein immunologically active subunits of an arthropod hemocyanin or arylphorin, are used.

9. Method as claimed in claim 8, wherein one of the subunits of the hemocyanins or arylphorins of arthropods having a molecular weight of about 70–80,000 are used.

10. Method as claimed in claim 9, wherein the subunits a, d, e or a combination thereof of the hemocyanin of Eurypelma californicum is used.

11. Method as claimed in claim 10, wherein a peptide fragment consisting of 23 amino acids is used, obtained by chymotryptic cleavage of the subunit a.

12. Method as claimed in claim 11, wherein the peptide fragment consisting of 23 amino acids is bound to hemocyanin from Carcinus, or to arylphorin from Calliphora.

13. Method as claimed in claim 1, wherein the arthropod hemocyanins, arylphorins, or the combination thereof are mixed with viruses or viral components, bacteria or bacterial components, fungi or fungal components or animal parasites or their components, or are chemically or physically coupled with them.

14. Method as claimed in claim 13, wherein the coupled substances are suitable for direct inoculation.

15. Method as claimed in claim 1, wherein the arthropod hemocyanin, arylphorin or combination thereof is physically or chemically coupled with antigens before application to increase the strength of the immune reaction.

16. Method as claimed in claim 15, wherein coupling takes place on meth-A-ascites fragments.

17. A method for influencing the immune system of a warm-blooded animal by enhancing the activity of or proliferation of cytotoxic cells, comprising administering to a warm-blooded animal a cytotoxic cell-enhancing amount of (A) an arthropod hemocyanin or arylphorin preparation which is at least about 95% pure, or of (B) a preparation of immunologically active and cytotoxic cell-enhancing fragment of an arthropod hemocyanin or arylphorin which preparation is at least about 95% pure, in admixture with or chemically or physically coupled with one or more members of the group consisting of viruses, viral components, bacteria, bacterial components, fungi, fungal components, and animal parasites or components thereof.

18. A method for influencing the immune system of a warm-blooded animal by enhancing the activity of or proliferation of cytotoxic cells, comprising administering to a warm-blooded animal a cytotoxic cell-enhancing amount of an arthropod hemocyanin or arylphorin preparation which is at least about 95% pure.

19. A method according to claim 18 wherein the hemocyanin or arylphorin preparation is about 100% pure.

20. A method for influencing the immune system of a warm-blooded animal by enhancing the activity of or proliferation of cytotoxic cells, comprising administering to a warm-blooded animal a cytotoxic cell-enhancing amount of an immunologically active and cytotoxic cell-enhancing fragment of an arthropod hemocyanin or arylphorin.

21. A method according to claim 20 wherein the fragment has a molecular weight of from about 70–80,000.

22. A method according to claim 20 wherein the fragment is administered in the form of a preparation which is at least about 95% pure.

23. A method according to claim 20 wherein the fragment is subunit a, d or e, or a combination of one or more thereof, of *Eurypelma californicum* hemocyanin.

24. A method according to claim 20 wherein the fragment is the 23-amino acid fragment obtained by the chymotryptic cleavage of the a fragment of *Eurypelma californicum* hemocyanin.

25. A method according to claim 24 wherein the fragment is bound to an arthropod hemocyanin or arylphorin.

26. A method according to claim 24 wherein the fragment is bound to Carcinus or Octopus hemocyanin or the Calliphora arylphorin.

27. A method according to claim 17 wherein the hemocyanin or arylphorin is coupled to an antigen.

28. A method according to claim 19 wherein the hemocyanin or arylphorin is coupled to an antigen.

29. A method according to claim 17 wherein the hemocyanin or arylphorin is coupled to a fragment of a meth-A-sarcoma cell.

30. A method according to claim 19 wherein the hemocyanin or arylphorin is coupled to a meth-A-sarcoma cell.

31. A method according to claim 17 wherein the hemocyanin or arylphorin is isolated from tissue of an arthropod selected from the group consisting of Eurypelma, Limulus, Astacus, Carcinus and Calliphors.

32. A method according to claim 17 wherein the hemocyanin is *Eurypelma californicum* hemocyanin.

33. A method according to claim 19 wherein the hemocyanin is *Eurypelma californicum* hemocyanin.

34. A method according to claim 17 wherein the hemocyanin is *Astacus fluviatilis* hemocyanin.

35. A method according to claim 19 wherein the hemocyanin is *Astacus fluviatilis* hemocyanin.

36. A method according to claim 17 wherein the hemocyanin is *Carcinus maenas* hemocyanin.

37. A method according to claim 19 wherein the hemocyanin is *Carcinus maenas* hemocyanin.

38. A method according to claim 17 wherein the hemocyanin is *Limulus polyphemus* hemocyanin.

39. A method according to claim 19 wherein the hemocyanin is *Limulus polyphemus* hemocyanin.

40. A method according to claim 17 wherein the arylphorin is *Calliphora erythrocephala* arylphorin.

41. A method according to claim 19 wherein the arylphorin is *Calliphora erythrocephala* arylphorin.

42. A method for the treatment of tumors of a warm-blooded animal, comprising administering to a warm-blooded animal a therapeutically effective amount of an arthropod hemocyanin or arylphorin preparation which is at least about 95% pure.

43. A method for the treatment of tumors of a warm-blooded animal, comprising administering to a warm-blooded animal a therapeutically effective amount of a preparation of a an immunologically active and cytotoxic cell-enhancing fragment of an arthropod hemocyanin or arylphorin, which preparation is at least about 95% pure.

44. A composition for the treatment of tumors of a warm-blooded animal, comprising a therapeutically effective amount of an immunologically active and cytotoxic cell-enhancing fragment of an arthropod hemocyanin or arylphorin which is at least about 95% pure.

45. A composition for the treatment of tumors of a warm-blooded animal, comprising a therapeutically effective amount of an arthropod hemocyanin or arylphorin preparation, other than keyhole-limpet hemocyanin, which is at least about 95% pure.

46. A composition for influencing the immune system of a warm-blooded animal by enhancing the activity of or proliferation of cytotoxic cells, comprising a cytotoxic cell-enhancing amount of an arthropod hemocyanin or arylphorin preparation which is at least about 95% pure.

47. A composition for influencing the immune system of a warm-blooded animal by enhancing the activity of or proliferation of cytotoxic cells, comprising a cytotoxic cell-enhancing amount of an immunologically active and cytotoxic cell-enhancing fragment of an arthropod hemocyanin or arylphorin preparation which is at least about 95% pure.

* * * * *

UNITED STATES PATENT AND TRADEMARK OFFICE
CERTIFICATE OF CORRECTION

PATENT NO. : 5,231,081

DATED : July 27, 1993

INVENTOR(S) : Thomas Stiefel et al.

It is certified that error appears in the above-identified patent and that said Letters Patent is hereby corrected as shown below:

Col. 5, line 21, "c" should be --g--.

Col. 6, line 8, "EDT.A" should be --EDTA--.

Col. 6, line 34, "7" should be --+7--.

Col. 8, line 21, do not start a new paragraph.

Col. 8, line 22, "Carbohydrate Research" should be --*Carbohydrate Research*--.

Col. 11, line 18, "17" should be --18--.

Col. 11, line 20, "19" should be --20--.

Col. 11, line 22, "17" should be --18--.

Col. 11, line 25, "19" should be --20--.

Col. 11, line 29, "17" should be --18--.

Col. 11, line 32, "Calliphors" should be --Calliphora--.

Col. 11, line 33, "17" should be --18--.

Col. 11, line 35, "19" should be --20--.

Col. 11, line 37, "17" should be --18--.

Col. 11, line 39, "19" should be --20--.

Col. 11, line 41, "17" should be --18--.

UNITED STATES PATENT AND TRADEMARK OFFICE
CERTIFICATE OF CORRECTION

PATENT NO. : 5,231,081
DATED : July 27, 1993
INVENTOR(S) : Thomas Stiefel et al.

It is certified that error appears in the above-identified patent and that said Letters Patent is hereby corrected as shown below:

Col. 11, line 43, "19" should be --20--.

Col. 12, line 1, "17" should be --18--.

Col. 12, line 3, "19" should be --20--.

Col. 12, line 5, "17" should be --18--.

Col. 12, line 7, "19" should be --20--.

Signed and Sealed this

Nineteenth Day of April, 1994

BRUCE LEHMAN

Attest:

Attesting Officer

Commissioner of Patents and Trademarks